US012760266B2

(12) United States Patent
Imamura et al.

(10) Patent No.: US 12,760,266 B2
(45) **Date of Patent: *Oct. 13, 2026**

(54) METHOD OF PRODUCING BIOLOGICAL MATERIAL

(71) Applicant: NTT, Inc., Tokyo (JP)

(72) Inventors: Sosuke Imamura, Musashino (JP); Kazuhiro Takaya, Musashino (JP)

(73) Assignee: NTT, Inc., Tokyo (JP)

( * ) Notice: Subject to any disclaimer, the term of this patent is extended or adjusted under 35 U.S.C. 154(b) by 342 days.

This patent is subject to a terminal disclaimer.

(21) Appl. No.: 18/561,070

(22) PCT Filed: Jun. 15, 2021

(86) PCT No.: PCT/JP2021/022698

§ 371 (c)(1),
(2) Date: Nov. 15, 2023

(87) PCT Pub. No.: WO2022/264266

PCT Pub. Date: Dec. 22, 2022

(65) Prior Publication Data

US 2024/0263128 A1 Aug. 8, 2024

(51) Int. Cl.

*C12N 1/12* (2026.01)
*C12P 7/64* (2022.01)
*C12P 19/04* (2006.01)

(52) U.S. Cl.

CPC .................. *C12N 1/12* (2013.01); *C12P 7/64* (2013.01); *C12P 19/04* (2013.01); *C12N 2500/30* (2013.01)

(58) Field of Classification Search

None

See application file for complete search history.

(56) References Cited

PUBLICATIONS

Dirk Steinhauser, Alisdair R. Fernie, Wagner L. Araújo, "Unusual cyanobacterial TCA cycles: not broken just different", Trends in Plant Science, vol. 17, Issue 9, 2012, pp. 503-509, ISSN 1360-1385, https://doi.org/10.1016/j.tplants.2012.05.005. (Year: 2012).*

Chin, R., Fu, X., Pai, M. et al. The metabolite α-ketoglutarate extends lifespan by inhibiting ATP synthase and TOR. Nature 510, 397-401 (2014). https://doi.org/10.1038/nature13264 (Year: 2014).*

Imamura S, Kawase Y, Kobayashi I, Sone T, Era A, Miyagishima SY, Shimojima M, Ohta H, Tanaka K. Target of rapamycin (TOR) plays a critical role in triacylglycerol accumulation in microalgae. Plant Mol Biol. Oct. 2015;89(3):309-18. doi: 10.1007/s11103-015-0370-6. Epub Sep. 8, 2015. PMID: 26350402. (Year: 2015).*

Prioretti, L et al.. The inhibition of TOR in the model diatom Phaeodactylum tricornutum promotes a get-fat growth regime. Algal Research—Biomass, Biofuels and Bioproducts, 2017, 26, pp. 265-274. 10.1016/j.algal.2017.08.009. (Year: 2017).*

Forchhammer K, Selim KA. Carbon/nitrogen homeostasis control in cyanobacteria. FEMS Microbiol Rev. Jan. 1, 2020;44(1):33-53. doi: 10.1093/femsre/fuz025. PMID: 31617886; PMCID: PMC8042125. (Year: 2020).*

Takusagawa et al., "Primitive red alga *Cyanidioschyzon merolae* accumulates storage glucan and triacylglycerol under nitrogen depletion", The Journal of General and Applied Microbiology, vol. 62, No. 3, 2016, pp. 111-117.

Jüppner et al., "The target of rapamycin kinase affects biomass accumulation and cell cycle progression by altering carbon/nitrogen balance in synchronized Chlamydomonas reinhardtii cells", The Plant Journal, vol. 93, No. 2, 2018, pp. 355-376.

Imamura et al., "TOR (target of rapamycin) is a key regulator of triacylglycerol accumulation in microalgae" Plant Signaling & Behavior, vol. 11, No. 3, e1149285, 2016, pp. e1149285-1-e1149285-4.

Notification of Transmittal of Translation of the International Preliminary Report on Patentability mailed Dec. 28, 2023 in International Patent Application No. PCT/JP2021/022698, 6 pages. (Submitting English translation only.).

* cited by examiner

*Primary Examiner* — Melenie L Gordon
*Assistant Examiner* — John Paul Selwanes
(74) *Attorney, Agent, or Firm* — XSENSUS LLP

(57) ABSTRACT

A technique capable of achieving production of a biological material using photosynthetic microorganisms at low cost is provided. A method of producing a biological material includes culturing a photosynthetic microorganism in a culture medium containing dimethyl 2-oxoglutarate, and then collecting a substance produced by or accumulated in the photosynthetic microorganism.

7 Claims, 5 Drawing Sheets

METHOD OF PRODUCING BIOLOGICAL MATERIAL

CROSS-REFERENCE TO RELATED APPLICATION

The present application is based on PCT filing PCT/JP2021/022698, filed Jun. 15, 2021, the entire contents of which are incorporated herein by reference.

TECHNICAL FIELD

The present invention relates to a method of producing a biological material.

BACKGROUND ART

Most algae increase an amount of accumulated fat and oil and carbohydrate such as starch in an environment with lacking nutrients, e.g. nitrogen (Non-Patent Literature 1). The fat and oil produced by algae can be utilized as a raw material for biofuel, for example. In addition, carbohydrates produced by algae can be used as a raw material for, for example, fuel additives, pharmaceuticals, cosmetics and plastic products.

Accumulation of fat and oil and carbohydrate by algae can be promoted without causing nitrogen to be lacking in the environment. For example, accumulation of fat and oil and carbohydrates by algae can be promoted by using a target of rapamycin (TOR) inhibitor that specifically inhibits the activity of TOR kinase possessed by microalgae that are eukaryotic algae (Non-Patent Literatures 2 and 3).

CITATION LIST

Non-Patent Literature

Non-Patent Literature 1: Primitive red alga Cyanidioschyzon merolae accumulates storage glucan and triacylglycerol under nitrogen depletion. Mari Takusagawa, Yohei Nakajima, Takafumi Saito, Osami Misumi. J Gen Appl Microbiol, July 2016, 14:62(3):111-7.

Non-Patent Literature 2: The target of rapamycin kinase affects biomass accumulation and cell cycle progression by altering carbon/nitrogen balance in synchronized *Chlamydomonas reinhardtii* cells. Jessica Juppner, Umarah Mubeen, Andrea Leisse, Camila Caldana, Andrew Wiszniewski, Dirk Steinhauser, Patrick Giavalisco. Plant J. January 2018; 93(2):355-376.

Non-Patent Literature 3: Target of rapamycin (TOR) is a key regulator of triacylglycerol accumulation in microalgae. Sousuke Imamura, Yasuko Kawase, Ikki Kobayashi, Mie Shimojima, Hiroyuki Ohta, Kan Tanaka. Plant Signal Behav. 2016; 11(3):e1149285.

SUMMARY OF INVENTION

An object of the present invention is to provide a technique capable of achieving production of a biological material using photosynthetic microorganisms at low cost.

According to a first aspect of the present invention, there is provided a method of producing a biological material, including culturing a photosynthetic microorganism in a culture medium containing dimethyl 2-oxoglutarate and then collecting a substance produced by or accumulated in the photosynthetic microorganism.

According to a second aspect of the present invention, there is provided a method of producing a biological material, including culturing a photosynthetic microorganism in a culture medium, then adding dimethyl 2-oxoglutarate to the culture medium to continue the culture of the photosynthetic microorganism in the culture medium, and then collecting a substance produced by or accumulated in the photosynthetic microorganism.

According to a third aspect of the present invention, there is provided a promoter for use in promoting accumulation of a substance by a photosynthetic microorganism, containing dimethyl 2-oxoglutarate.

According to the present invention, there is provided a technique capable of achieving production of a biological material using photosynthetic microorganisms at low cost.

DESCRIPTION OF EMBODIMENTS

Figure 1:
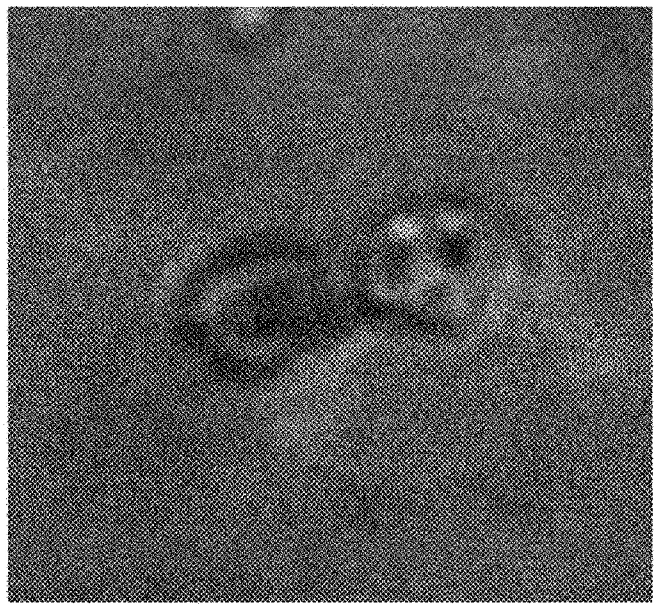
FIG. 1 shows a bright field image obtained using a microscope for unicellular red algae cultured in a culture medium added with a promoter.

Hereinafter, embodiments of the present invention will be described. The embodiments described below are more specific implementations of any of the above-mentioned aspects. The items described below can be incorporated into each of the above-mentioned aspects alone or in combination.

In a method of producing a biological material according to an embodiment of the present invention, first, photosynthetic microorganisms are cultured in a culture medium. In this culture, the photosynthetic microorganisms are irradiated with light, for example, in the presence of carbon dioxide. For example, the photosynthetic microorganisms are irradiated with sunlight under the air atmosphere. This causes photosynthesis in the photosynthetic microorganisms and causes the photosynthetic microorganisms to proliferate.

The photosynthetic microorganisms are, for example, microorganisms that carry out oxygenic photosynthesis. The photosynthetic microorganisms are, for example, algae such as eukaryotic algae. The algae are preferably microalgae. Here, "microalgae" are, for example, photosynthetic eukaryotes, and is a unicellular organism or a colony thereof. The microalgae are, for example, unicellular green algae such as *Chlamydomonas reinhardtii* and *Botryococcus*, unicellular red algae such as Cyanidioschyzon merolae, or a colony thereof. The photosynthetic microorganisms may not be a eukaryote. The photosynthetic microorganisms may be a prokaryotic organism, for example, bacteria such as cyanobacterium. The prokaryotic organisms may be archaea.

As the culture medium, a culture medium containing all nutrients necessary for the proliferation and photosynthesis of photosynthetic microorganisms in a sufficient concentration is used. The culture medium is, for example, a liquid culture medium.

The above-mentioned cultivation is, for example, suspended cultivation. The above-mentioned cultivation may be another type of cultivation, e.g., attached cultivation. In attached cultivation, a biofilm of photosynthetic microorganisms is formed on a support, and the cultivation is carried out in a state where the biofilm and the culture medium are brought into contact with each other.

Next, a promoter to promote accumulation of a substance by photosynthetic microorganisms is added to the above-mentioned culture medium. Then, the cultivation of the photosynthetic microorganisms is continued in the culture medium. In other words, the photosynthetic microorganisms are irradiated with light, for example, in the presence of carbon dioxide. For example, the photosynthetic microorganisms are irradiated with sunlight under the air atmosphere.

The promoter contains dimethyl 2-oxoglutarate represented by the following chemical formula (1). Dimethyl 2-oxoglutarate slows cell proliferation of photosynthetic microorganisms, thereby promoting accumulation of substances produced by the photosynthetic microorganisms.

Chemical Formula (1)

[C1]

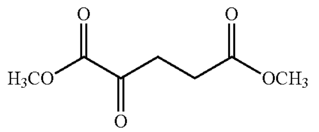

The promoter may further contain a solvent. As the solvent, for example, a liquid having the same or almost the same composition as that of the culture medium used for culturing the photosynthetic microorganisms can be used. When dimethyl 2-oxoglutarate is diluted with a solvent, for example, dimethyl 2-oxoglutarate can be supplied uniformly to photosynthetic microorganisms.

The substances produced and accumulated by the photosynthetic microorganisms are various, such as fat and oil, carbohydrates, hydrocarbons, amino acids, and the like. The substances produced by and accumulated in the photosynthetic microorganisms are different according to the kind of the photosynthetic microorganisms. The fat and oil are, for example, neutral lipids such as triacylglycerols. The hydrocarbons are, for example, botryococcene. The carbohydrates are, for example, starch or a combination of starch and one or more other carbohydrate components.

A timing at which the promoter is added is determined based on any of, for example, a light transmittance and turbidity of a dispersion containing the photosynthetic microorganisms and the culture medium, the number of cells per volume, a specific growth rate of the photosynthetic microorganisms and a rate of change thereof. According to one example, a timing at which the promoter is added is determined by comparing any of a light transmittance and turbidity of a dispersion, the number of cells per volume, a specific growth rate of the photosynthetic microorganisms and a rate of change thereof with a predetermined threshold.

The addition of the promoter to the culture medium is preferably performed so that the number of cells of the photosynthetic microorganisms per volume immediately before the addition of the promoter is within the range of 100,000 to 10,000,000,000 cells/mL, and more preferably performed so that the number of cells of the photosynthetic microorganisms per volume is within the range of 10,000,000 to 100,000,000 cells/mL. Here, the number of cells of the photosynthetic microorganisms per volume is the ratio of the number of cells of the photosynthetic microorganisms to the total volume of the photosynthetic microorganisms and the culture medium.

In order to efficiently produce the biological material, it is desirable that the number of cells of the photosynthetic microorganisms be large to some extent. However, when the photosynthetic microorganisms proliferate excessively, hardly any light reaches a part deep inside thereof.

The promoter is preferably added so that the dimethyl 2-oxoglutarate concentration of a mixed liquid containing the culture medium, the photosynthetic microorganisms, and the promoter is in the range of 0.001 to 1,000 mmol/L, and more preferably added so that the concentration is in the range of 0.5 to 5 mmol/L. When the concentration is lowered, the effect of promoting the accumulation of the substances in the photosynthetic microorganisms is reduced. When the concentration is increased, the cost becomes higher.

The cultivation period after the addition of the promoter is different according to the kind of the photosynthetic microorganisms. In general, the cultivation period is preferably in the range of 3 hours to 14 days, and more preferably in the range of 12 hours to 72 hours.

Thereafter, the substances produced by or accumulated in the photosynthetic microorganisms are collected. When the substances accumulated by the photosynthetic microorganisms in the cell are collected, for example, hydrophobic substances are extracted from the photosynthetic microorganisms to obtain the extract containing the hydrophobic substances and the residue containing hydrophilic substances. Alternatively, the hydrophilic substances are extracted from the photosynthetic microorganisms to obtain an extract containing the hydrophilic substances and a residue containing the hydrophobic substances. When substances produced by the photosynthetic microorganisms and released to the outside of the cells are collected, the substances are collected from, for example, a culture medium. Here, as an example, a method for acquiring fat and oil or carbohydrates from the photosynthetic microorganisms will be described.

For example, the photosynthetic microorganisms are first separated from the culture medium. In the case of suspended cultivation, at least a part of the culture medium is removed from the mixed solution of the photosynthetic microorganisms and the culture medium, for example, by means of centrifugal separation or compression. Thereby, a concentrate containing photosynthetic microorganisms in a higher concentration than the previous mixed liquid is obtained. Then, the concentrate is dried to obtain a dried product composed of the photosynthetic microorganisms.

Next, fat and oil are extracted from the dried product composed of the photosynthetic microorganisms. An organic solvent is used as an extraction medium for extracting the fat and oil. Thus, the extract containing the fat and oil is obtained and the residue containing carbohydrates is obtained.

In the case of producing fat and oil, the extract is then purified if necessary. The purified product may be modified. In this way, fat and oil are obtained from photosynthetic microorganisms. The fat and oil thus obtained can be used as a biofuel or a raw material thereof, for example.

In the case of producing a carbohydrate, for example, a carbohydrate is extracted from the above residue. In the case of extracting polysaccharides such as starch, for example, water is used as the extraction medium. Then, if necessary, the extract is purified. The purified product may be modified. In this way, carbohydrates are obtained from photosynthetic microorganisms. The carbohydrates can be used as a raw material for, for example, fuel additives, pharmaceuticals, cosmetics, and plastic products.

For example, fat and oil, carbohydrates, or a purified product or a modified product thereof can be obtained in the above-described method. In addition, using a method similar thereto, other substances such as hydrocarbons and amino acids accumulated in the photosynthetic microorganisms, or a purified product or modified products thereof can be obtained.

The substances produced by or accumulated in the photosynthetic microorganisms and acquired as described above, substances obtained by performing post-treatment such as purification and modification to the above substances, or substances obtained by using the above substances as raw materials are biological materials. The biological material may be a product, for example, a biofuel, a fuel additive, a pharmaceutical, a supplement, a physiologically active substance, a food, a cosmetic, or a plastic product. Alternatively, the biological material is one or more components or raw materials of the above-mentioned products.

As described above, the accumulation of substances in the photosynthetic microorganisms can be promoted by reducing nitrogen in the environment. However, in order to change an environment from one in which all nutrients are sufficiently present to one in which a specific nutrient is deficient, for example, a culture medium in which all nutrients are sufficiently present needs to be replaced with one in which a specific nutrient is deficient. In order to replace a culture medium used for culturing photosynthetic microorganisms, it is necessary to collect the photosynthetic microorganisms by using a centrifugal separator or the like. Therefore, in order to produce a biological material using photosynthetic microorganisms on a large scale, a large amount of energy, time and effort are required.

If a TOR inhibitor is used, exchange of a culture medium for changing the environment from one in which all nutrients are sufficiently present to one in which a specific nutrient is deficient is unnecessary. However, TOR inhibitors are expensive.

In the method described above, the cell proliferation of the photosynthetic microorganism slows by adding a promoter to the culture medium, thereby promoting the accumulation of substances in the photosynthetic microorganisms. That is, in this method, there is no need to exchange the culture medium for changing the environment from one in which all nutrients are sufficiently present to one in which a particular nutrient is deficient.

The promoter used in this method contains dimethyl 2-oxoglutarate as an active ingredient. Dimethyl 2-oxoglutarate is much cheaper than a TOR inhibitor.

For this reason, the method can realize production of a biological material using photosynthetic microorganisms at low cost.

The TOR inhibitor is not effective for all photosynthetic microorganisms. On the other hand, dimethyl 2-oxoglutarate is a derivative of 2-oxoglutarate represented by the following chemical formula (2). 2-Oxoglutarate is a metabolite common to all organisms. Therefore, the above-described effects of the addition of the promoter containing dimethyl 2-oxoglutarate can be exhibited in all photosynthetic microorganisms.

Chemical Formula (2)

[C2]

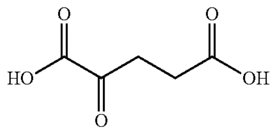

[Tests]

The tests conducted by the inventors will be described below.

(Test 1)

Unicellular red algae were cultured in suspension under a light condition and a promoter was added thereto. An MA2 culture medium was used as a culture medium. Cyanidioschyzon merolae were used as unicellular red algae. Dimethyl 2-oxoglutarate was used as a promoter. The promoter was added so that the final concentration of dimethyl 2-oxoglutarate would be 2 mmol/L.

After the addition of the promoter, the cultivation was continued for 24 hours more. Thereafter, a bright field image was obtained for the cultured unicellular red algae using a microscope. In addition, the fat and oil of the unicellular red algae were stained with commercially available BODIPY® from the Cosmo Bio, Inc. Then, a fluorescence observation image of the unicellular red algae with stained fat and oil was acquired by using a fluorescence microscope In addition, cultivation was similarly conducted as described above except that no promoter was added. Then, acquisition of a bright field image, staining of fat and oil, and acquisition of a fluorescence observation image were carried out also for the cultured unicellular red algae.

Figure 2:
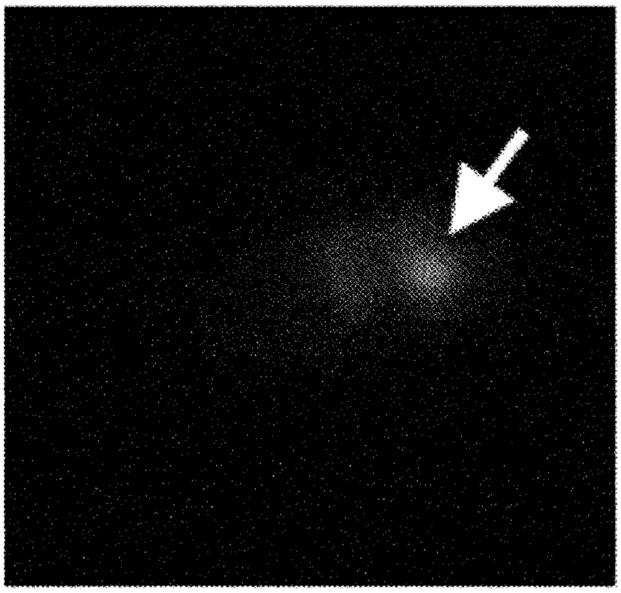
FIG. 2 shows a fluorescence observation image obtained using a microscope for unicellular red algae cultured in the culture medium added with the promoter and having fat and oil stained.
Figure 3:
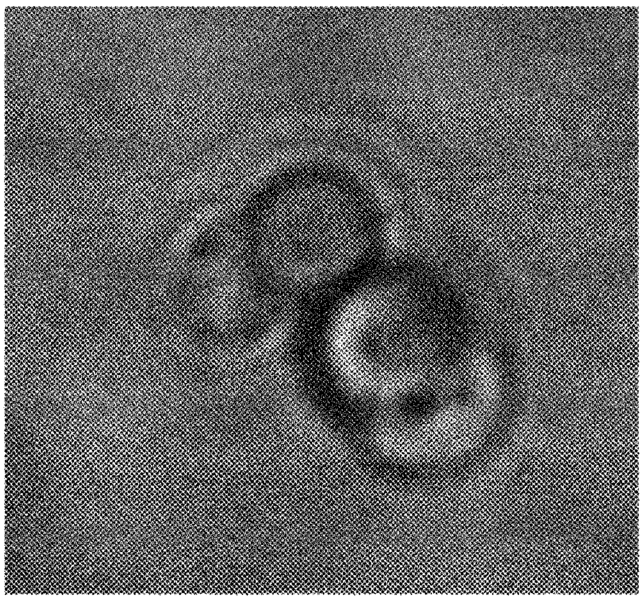
FIG. 3 shows a bright field image obtained using a microscope for unicellular red algae cultured in a culture medium without adding a promoter thereto.
Figure 4:
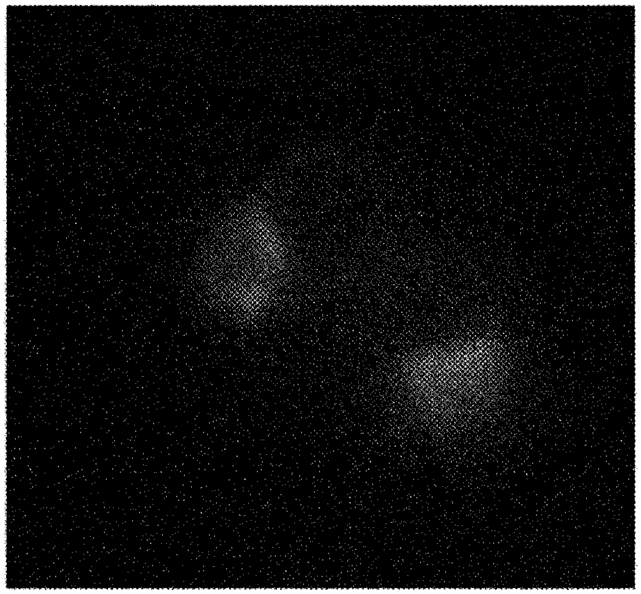
FIG. 4 shows a fluorescence observation image obtained using a microscope for unicellular red algae cultured in the culture medium without adding the promoter and having fat and oil stained.

FIG. 1 shows a bright field image obtained using a microscope for the unicellular red algae cultured in the culture medium added with the promoter. FIG. 2 shows a fluorescence observation image obtained using a microscope for the unicellular red algae cultured in the culture medium added with the promoter and having fat and oil stained. FIG. 3 shows a bright field image obtained using a microscope for the unicellular red algae cultured in the culture medium without adding a promoter thereto. FIG. 4 shows a fluorescence observation image obtained using a microscope for the unicellular red algae cultured in the culture medium without adding a promoter and having fat and oil stained.

As shown in FIG. 4, almost no fluorescence caused by staining was observed in the unicellular red algae cultured without adding a promoter. On the other hand, a region emitting strong fluorescence due to staining (the region indicated by the arrow) was observed in the unicellular red algae cultured with the promoter added thereto as shown in FIG. 2. That is, it was confirmed that accumulation of fat and oil was greatly promoted due to addition of the promoter.

(Test 2)

The same cultivation as in test 1 was performed, and the amount of starch contained in the unicellular red algae after the cultivation was determined. The results are shown in FIG. 5.

Figure 5:
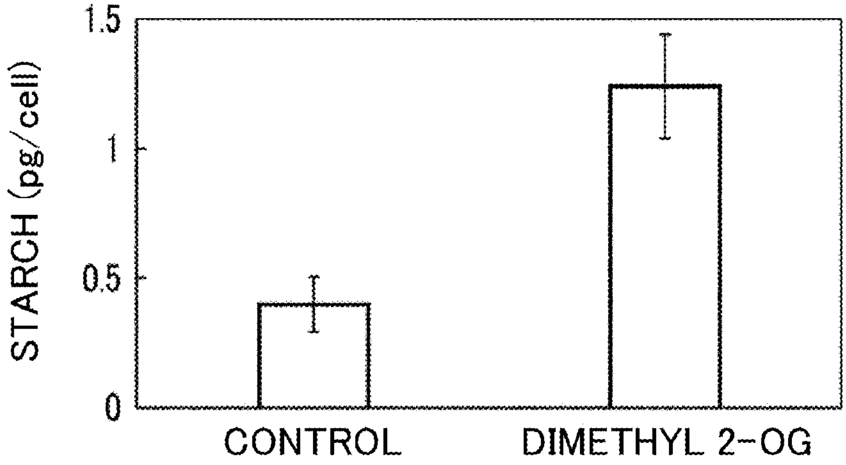
FIG. 5 is a graph showing an example of the influence of the addition of a promoter on the amount of accumulation of starch.

FIG. 5 is a graph showing an example of the influence of addition of a promoter on the amount of accumulation of starch. FIG. 5 shows the average of the results of three independent tests and the standard deviation. In FIG. 5, "control" represents the results obtained for the unicellular red algae cultured without adding a promoter to the culture medium. In addition, "dimethyl 2-OG" represents the results obtained for the unicellular red algae cultured in the culture medium with a promoter added thereto.

As shown in FIG. 5, the unicellular red algae cultured with the addition of the promoter exhibits a significantly greater amount of accumulation of starch than that of the unicellular red algae cultured without adding a promoter. From this result, it was confirmed that the addition of the promoter greatly promoted the accumulation of starch.

The invention claimed is:

1. A method of promoting accumulation of a fat-based, oil based, and starch-based biological material, comprising:

culturing Cyanidioschyzon merolae in a culture medium containing dimethyl 2-oxoglutarate with irradiation of light; and then collecting the fat-based, oil based, and starch-based biological material.

2. The method of claim 1, wherein the dimethyl 2-oxoglutarate is at a concentration of 0.001 to 1,000 mmol/L.

3. The method of claim 1, wherein the collecting of the fat-based, oil based, and starch-based biological material includes extracting one of a hydrophobic substance and a hydrophilic substance from the Cyanidioschyzon merolae to obtain an extract and a residue.

4. A method of promoting accumulation of a fat-based, oil based, and starch-based biological material, comprising:

culturing Cyanidioschyzon merolae in a culture medium;

then adding dimethyl 2-oxoglutarate to the culture medium and thereafter continuing the culture of the Cyanidioschyzon merolae in the culture medium with irradiation of light; and then collecting the fat-based, oil based, and starch-based biological material.

5. The method of claim 4, wherein a concentration of the Cyanidioschyzon merolae is 100,000 to 1,000,000,000,000 cells/mL immediately before adding the dimethyl 2-oxoglutarate.

6. The method of claim 4, wherein the dimethyl 2-oxoglutarate is at a concentration of 0.001 to 1,000 mmol/L.

7. The method of claim 4, wherein the collecting of the fat-based, oil based, and starch-based biological material includes extracting one of a hydrophobic substance and a hydrophilic substance from the Cyanidioschyzon merolae to obtain an extract and a residue.

* * * * *